(12) United States Patent  (10) Patent No.: US 7,666,308 B2
Scholtens et al.  (45) Date of Patent: Feb. 23, 2010

(54) MAGNETIC SEPARATION APPARATUS AND METHODS

(75) Inventors: Tycho M. Scholtens, Enschede (NL); Leon L. M. M. Terstappen, Huntingdon Valley, PA (US); Arjan G. J. Tibbe, Deventer (NL)

(73) Assignee: Veridex, LLC., Raritan, NJ (US)

( * ) Notice: Subject to any disclaimer, the term of this patent is extended or adjusted under 35 U.S.C. 154(b) by 490 days.

(21) Appl. No.: 11/447,562

(22) Filed: Jun. 6, 2006

(65) Prior Publication Data

US 2006/0257847 A1  Nov. 16, 2006

Related U.S. Application Data

(60) Continuation-in-part of application No. 10/733,829, filed on Dec. 10, 2003, now Pat. No. 6,890,426, which is a division of application No. 10/602,979, filed on Jun. 24, 2003, now Pat. No. 6,790,366, which is a continuation-in-part of application No. 09/201,603, filed on Nov. 30, 1998, now Pat. No. 6,136,182, which is a continuation-in-part of application No. 08/867,009, filed on Jun. 2, 1997, now Pat. No. 5,985,153.

(60) Provisional application No. 60/019,282, filed on Jun. 7, 1996, provisional application No. 60/030,436, filed on Nov. 5, 1996.

(51) Int. Cl.
*B01D 35/06* (2006.01)
*C12Q 1/00* (2006.01)
*C12M 1/34* (2006.01)
*G01N 33/533* (2006.01)

(52) U.S. Cl. .................. 210/695; 210/94; 210/222; 436/164; 436/177; 436/526; 435/7.2; 435/288.7; 422/82.05; 209/213; 209/214; 209/223.1

(58) Field of Classification Search .................. 436/164, 436/177, 526; 435/7.2, 288.7; 422/82.05; 210/695, 94, 222; 209/213, 214, 223.1
See application file for complete search history.

(56) References Cited

U.S. PATENT DOCUMENTS

| 4,729,949 | A | 3/1988 | Weinreb et al. |
| 4,735,504 | A | 4/1988 | Tycko |
| 4,989,978 | A | 2/1991 | Groner |
| 5,030,560 | A | 7/1991 | Sinor et al. |
| 5,053,344 | A | 10/1991 | Zborowski et al. |
| 5,200,084 | A | 4/1993 | Liberti et al. |
| 5,340,749 | A | 8/1994 | Fujiwara et al. |
| 5,375,606 | A | 12/1994 | Slezak et al. |
| 5,411,863 | A | 5/1995 | Miltenyi |
| 5,428,451 | A | 6/1995 | Lea et al. |

(Continued)

FOREIGN PATENT DOCUMENTS

WO  WO 9411078 A1 * 5/1994

*Primary Examiner*—David A Reifsnyder

(57) ABSTRACT

Apparatuses and methods for separating, immobilizing, and quantifying biological substances from within a fluid medium. Biological substances are observed by employing a vessel (6) having a chamber therein, the vessel comprising a transparent collection wall (5). A high internal gradient magnetic capture structure may be on the transparent collection wall (5), magnets (3) create an externally-applied force for transporting magnetically responsive material toward the transparent collection wall (5). V-shaped grooves on the inner surface of the viewing face of the chamber provide uniform. The invention is also useful in conducting quantitative analysis and sample preparation in conjunction with automated cell enumeration techniques.

14 Claims, 9 Drawing Sheets

U.S. PATENT DOCUMENTS

| | | | |
|---|---|---|---|
| 5,451,525 A | 9/1995 | Shenkin et al. | |
| 5,466,574 A | 11/1995 | Liberti et al. | |
| 5,494,831 A | 2/1996 | Kindler | |
| 5,498,550 A | 3/1996 | Fujiwara et al. | |
| 5,541,072 A | 7/1996 | Wang et al. | |
| 5,646,001 A | 7/1997 | Terstappen et al. | |
| 5,985,153 A | 11/1999 | Dolan et al. | |
| 6,013,532 A | 1/2000 | Liberti et al. | |
| 6,790,366 B2 * | 9/2004 | Terstappen et al. | 210/695 |
| 6,890,426 B2 * | 5/2005 | Terstappen et al. | 210/94 |

\* cited by examiner

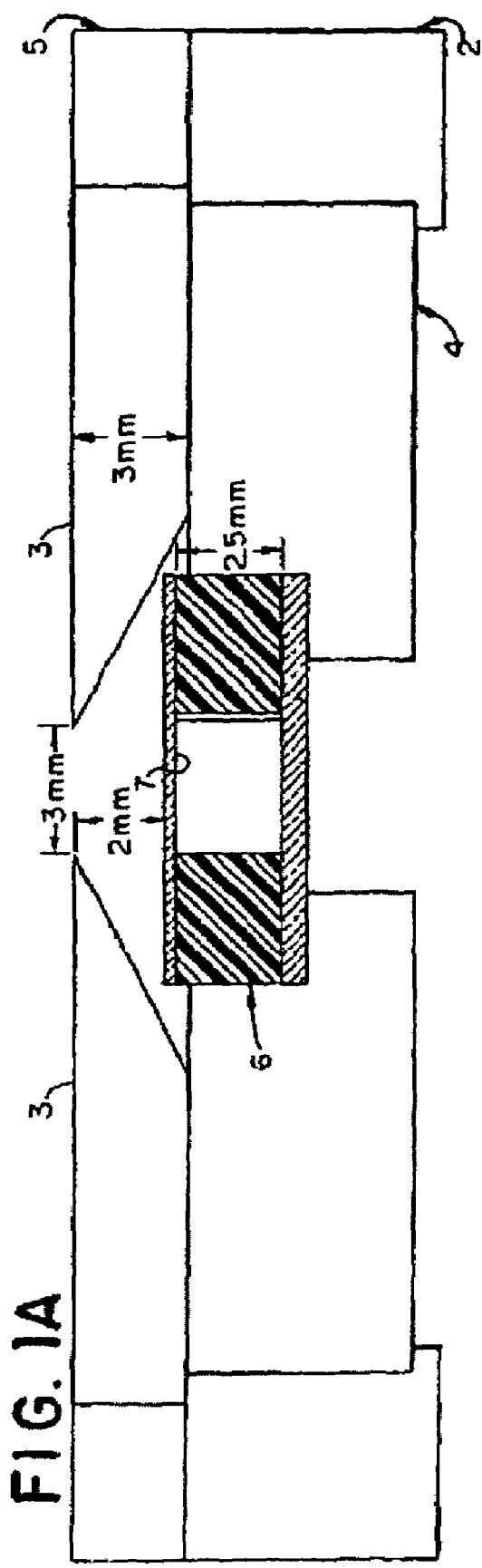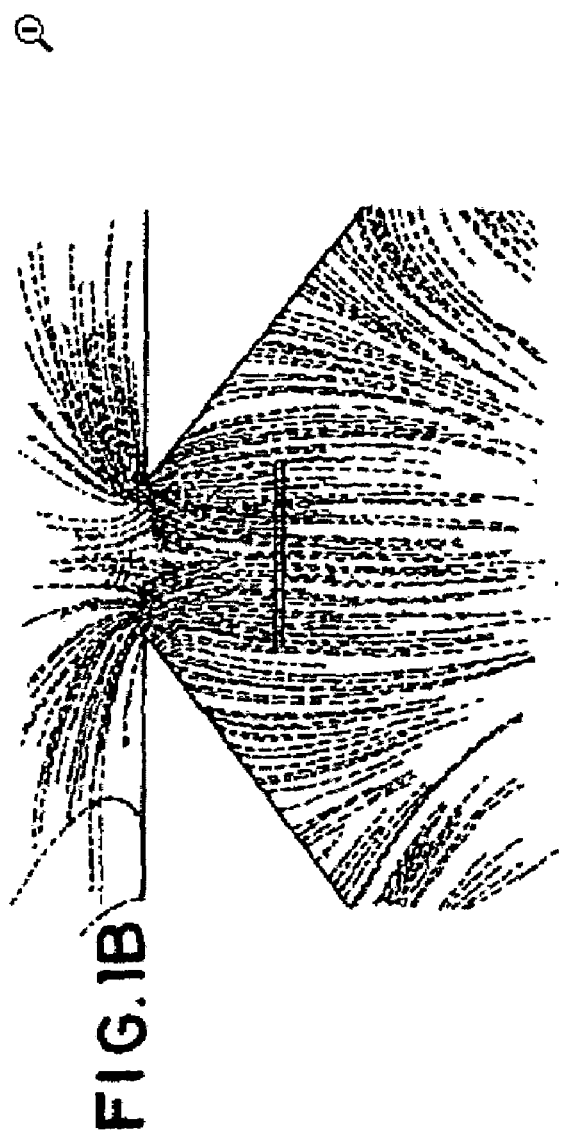
FIG. 1A
FIG. 1B (A)

(B)

MAGNETIC SEPARATION APPARATUS AND METHODS

CROSS-REFERENCE TO RELATED APPLICATIONS

This is a continuation-in-part of Ser. No. 10/733,829, filed on Dec. 10, 2003, now U.S Pat. No. 6,890,426, which is a division 10/602,979 filed Jun. 24, 2003 of U.S. Pat. No. 6,790,366, issued on Sep. 14, 2004, filed as a national application under 35 USC 371 from PCT/US99/28231, filed on Nov. 30, 1999, which is a continuation-in-part of U.S. application Ser. No. 09/201,603, filed Nov. 30, 1998, now U.S. Pat. No. 6,136,182 which is a continuation-in-part of U.S. application Ser. No. 08/867,009, filed Jun. 2, 1997, now U.S. Pat. No. 5,985,153, which claims the benefit of U.S. Provisional Application No. 60/019,282, filed Jun. 7, 1996, and claims the benefit of U.S. Provisional Application No. 60/030,436, filed Nov. 5, 1996. Application Ser. Nos. 11/434,321, filed on May 12, 2006,; U.S. Pat. Nos. 6,660,159, 6,136,182 and 5,985,153 are all incorporated in full by reference herein.

BACKGROUND

The present invention relates to improved apparatus and methods for performing qualitative and quantitative analysis of microscopic biological specimens. In particular, the invention relates to such apparatus and methods for isolating, collecting, immobilizing, and/or analyzing microscopic biological specimens or substances which are susceptible to immunospecific or non-specific binding with magnetic-responsive particles having a binding agent for producing magnetically-labeled species within a fluid medium. As used herein, terms such as "magnetically-labeled specimen" shall refer to such biological specimens or substances of investigational interest which are susceptible to such magnetic labeling.

U.S. Pat. No. 5,985,153 describes an apparatus and method wherein an external magnetic gradient is employed to attract magnetically labeled target specimens present in a collection chamber to one of its surfaces, and where an internal magnetic gradient is employed to obtain precise alignment of those specimens on that surface. The movement of magnetically labeled biological specimens to the collection surface is obtained by applying a vertical magnetic gradient to move the magnetically labeled biological specimens to the collection surface. The collection surface is provided with a ferromagnetic capture structure, such as plurality of ferromagnetic lines supported on an optically transparent (viewing) face of a sample chamber.

Once the magnetically labeled biological specimens are pulled sufficiently close to the surface by the externally applied gradient, they come under the influence of an intense local gradient produced by the ferromagnetic collection structure and are immobilized at positions laterally adjacent thereto. The local gradient preferably exceeds adhesion forces which can hold the biological specimens to the transparent surface after they collide with the surface. Alternatively, the adhesiveness of the surface must be sufficiently weak to allow the horizontal magnetic force to move the magnetically labeled biological specimens towards the ferromagnetic structures. The smoothness and the hydrophobic or hydrophilic nature of the surface are factors that can influence the material chosen for the collection surface or the treatment of this surface to obtain a slippery surface.

U.S. Ser. No. 10/733,829 and U.S. Pat. No. 6,790,366 describe methods and apparatus for separating, immobilizing, and quantifying biological substances in a fluid sample, incorporating the principles of the externally applied gradient described above, and further incorporate a high internal gradient magnetic capture structure on the transparent collection wall. The capture structure encourages a uniform alignment of caputred biological substances for quantitative analysis with automated enumeration techniques.

In accordance with the present invention, there are described further alternative embodiments and improvements for the collection chamber whereby the internal magnetic capture sturcture is used in conjunction with small V-shaped grooves on the fluid side of the optically transparent (viewing) face of the chamber to align the target specimens for automated optical analysis. A prefereed embodiment of the present invention replaces the internal magnetic capture structure with small V-shaped grooves on the fluid side of the optically transparent (viewing) face of the chamber, and with the optimum dilution of magnetically-labeled specimens provides an alignment surface for automated optical analysis. In both embodiments, magnetically-labeled specimens and unbound magnetic particles move toward the inner surface of the chamber's viewing face, under the influence of the externally applied magnetic gradient. When they approach the surface, they come in contact with the slope of the V-shaped groove, forcing the magnetically-labeled specimens and unbound magnetic particles to move to the top of the groove. At the top of the V-shaped groove is a small chimney-shaped component with a width of approximately 2 to 3 µm which stops the magneticall-labeled specimens and allows the unbound magnetic particles to move further up into the chimney structure and outside the focal plane, used in optical analysis. This allows for alignment of the cell population in a profile that allows easier scanning with minimization of non-homogenously illuminated cell and provides an image of the cells without the interferring ferrofluid. In the preferred embodiment, the need for internal magnetic capture structures, previously described, is not present, thus reducing the overall manufacturing cost of the viewing chamber.

BRIEF DESCRIPTION OF THE FIGURES

FIG. 1A is a schematic diagram of a magnetic separator.

FIG. 1B shows the magnetic field provided in the magnetic separator of FIG. 1A.

DETAILED DESCRIPTIONS

Figure 2A:
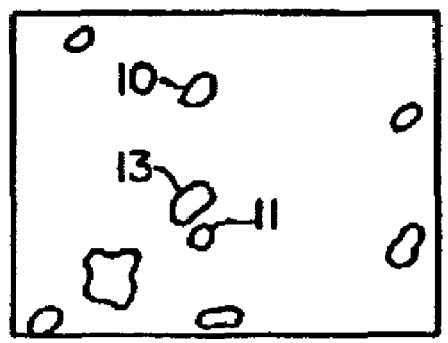
FIGS. 2A-C are microphotographs of specimens collected in a magnetic separator.

I. Vertical Gradient Collection and Observation of Target Specimens

Target specimens such as cells, cell debris, and cell components are collected against a collection surface of a vessel without subsequent alignment adjacent to a ferromagnetic collection structure. These cells include white blood cells, cells of epithelial origin, endothelial cells, fungal cells, and bacterial cells. The collection surface is oriented perpendicular to a magnetic field gradient produced by external magnets. In this embodiment, magnetic nanoparticles and magnetically labeled biological specimens are collected in a substantially homogeneous distribution on the optically transparent face of the chamber while non-selected entities remain below in the fluid medium. This result can be accomplished by placing a chamber in a gap between two magnets arranged as shown in FIG. 1A, such that the chamber's transparent collection surface is effectively perpendicular to a vertical field gradient generated by external magnets 3. The magnets 3 have a thickness of 3 mm, and are tapered toward a gap of 3 mm. The magnets 3 are held in a yoke 1, which rests atop a housing 2. A vessel support 4 holds the vessel 6 in a region between the magnets where the lines of magnetic force are directed substantially perpendicular to the collection surface 5 of the vessel 6. The collection surface of the vessel is preferably formed of a 0.1 mm thick polycarbonate member. The collection surface is parallel to, and 2 mm below, the upper surface of the external magnets 3. The space between the inner, top surface edges of the magnets is 3 mm.

The taper angle of the magnets 3 and the width of the gap between the two magnets determine the magnitude of the applied magnetic field gradient and the preferable position of the collection surface of the vessel. The field gradient produced by the magnets can be characterized as having a substantially uniform region, wherein the gradient field lines are substantially parallel, and fringing regions, wherein the gradient field lines diverge toward the magnets. FIG. 1B shows mathematically approximated magnetic field gradient lines for such a magnet arrangement. The magnetic field lines (not shown) are predominantly parallel to the chamber surface while the gradient lines are predominantly perpendicular to it. To collect a uniformly distributed layer of the target specimens, the vessel is positioned to place the chamber in the uniform region such that there are substantially no transverse magnetic gradient components which would cause lateral transport of the magnetically labeled biological specimens to the collection surface.

To illustrate the collection pattern of magnetic material on the collection surface area, a chamber with inner dimensions of 2.5 mm height (z), 3 mm width (x) and 30 mm length (y) was filled with 225 µl of a solution containing 150 nm diameter magnetic beads and placed in between the magnets as illustrated in FIG. 1A. The magnetic beads moved to the collection surface and were distributed evenly. When the vessel was elevated relative to the magnets, such that a significant portion of the top of the vessel was positioned in a fringing region, significant quantities of the magnetic particles parallel toward and accumulated at respective lateral areas of the collection surface positioned nearest the magnets.

In order to enhance uniformity of collection on the collection surface, the surface material can be selected or otherwise treated to have an adhesive attraction for the collected species. In such an adhesive arrangement, horizontal drifting of the collected species due to any deviations in positioning the chamber of deviations from the desired perpendicular magnetic gradients in the "substantially uniform" region can be eliminated.

Figure 2B:
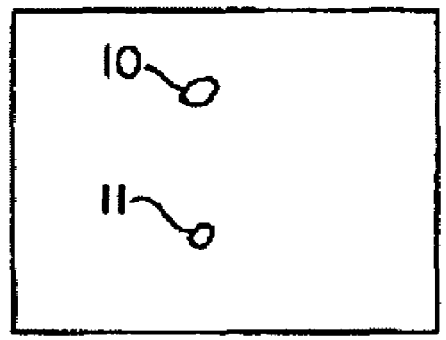
Figure 2C:
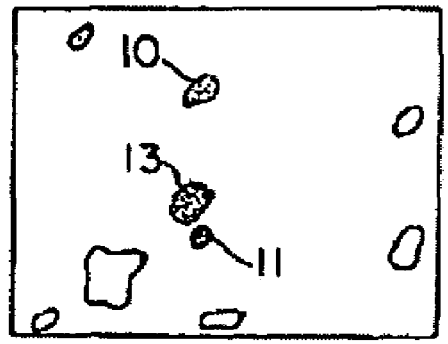

An example of the use of the present embodiment discussed device is a blood cancer test. Tumor derived epithelial cells can be detected in the peripheral blood. Although present at low densities, 1-1000 cells per 10 ml of blood, the cells can be retrieved and quantitatively analyzed from a sample of peripheral blood using an anti-epithelial cell specific ferrofluid. FIG. 2 illustrates an example of the use of the magnets and the chamber without the influence of a capture structure on the collection surface to localize, differentiate and enumerate peripheral blood selected epithelial derived tumor cells. In this example, 5 ml of blood was incubated with 35 µg of an epithelial cell specific ferrofluid (EPCAM-FF, Immunicon Corp., Huntingdon Valley, Pa.) for 15 minutes. The sample was placed in a quadrupole magnetic separator (QMS 17, Immunicon Corp.) for 10 minutes and the blood was discarded. The vessel was taken out of the separator and the collected cells present at the wall of the separation vessel were resuspended in a 3 ml of a buffer containing a detergent to permeabilize the cells (Immunoperm, Immunicon Corp.) and placed back in the separator for 10 minutes. The buffer containing the detergent was discarded and the vessel was taken out of the separator and the cells collected at the wall were resuspended in 200 µl of a buffer containing the UV excitable nucleic acid dye DAPI (Molecular Probes) and Cytokeratin monoclonal antibodies (identifying epithelial cells) labeled with the fluorochrome Cy3. The cells were incubated for 15 minutes after which the vessel was placed in the separator. After 5 minutes the uncollected fraction containing excess reagents was discarded, the vessel was taken out of the separator and the collected cells were resuspended in 200 µl of an isotonic buffer. This solution was placed into a collection chamber and placed in the magnetic separator shown in FIG. 1A. The ferrofluid labeled cells and the free ferrofluid particles moved immediately to the collection surface and were evenly distributed along the surface as is shown in FIG. 2A. The figure shows a representative area on the collection surface using transmitted light and a 20× objective. In FIG. 2B the same field is shown but now a filter cube is used for Cy3 excitation and emission. Two objects can be identified and are indicated with 1 and 2. FIG. 2C shows the same field but the filter cube is switched to one with an excitation and emission filter cube for DAPI. The objects at position 1 and 2 both stain with DAPI as indicated at positions 3 and 5 confirm their identity as epithelial cells. Additional non epithelial cells and other cell elements cells are identified by the DAPI stain; an example is indicated by the number 4.

II. V-Shaped Grooved as Collection Structures

To provide for spatially patterned collection of target specimens for qualitative and quantitative analysis of microscopic biologic samples, the present invention relates to making and using V-groove structures on the inner surface of the imaging chamber. Generally, V-grooves are long v-shaped grooves, pre-molded into the inner portion of the viewing surface on the imaging chamber. These structures provide an alignment of cells as good as or even better than previously reported Ni lines. Furthermore, V-grooves are made from a highly transparent material, optically suited for imaging the entire cell. A schematic drawing of the V-grooves together with the alignment principle of the Ni lines, for comparison, is shown in FIG. 3.

Figure 3:
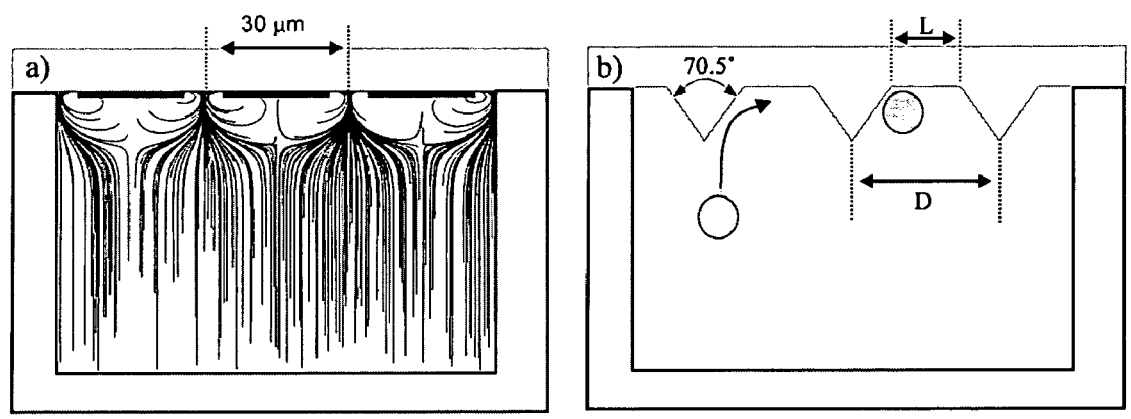
FIGS. 3A and 3B are alignment lines induced by the extra magnetic field from Ni lines (A) or V-shaped grooves (B), both in the presence of the external magnetic field. Values D and L are the main parameters of the capture structure. L is the length of the flat horizontal area and D is the spacing of the grooves. The angle of 70.5° is described for the V-groove design shown, but it is understood that any angle design may be appropriate.

FIG. 3 illustrates the principle of cell alignment using V-grooves. Magnetically induced cell movement in the chamber is similar to Ni lines, except at the inner surface of the sample chamber. Here, the magnetically labeled cells will either collide with the inclined surface of the V-grooves and slide into the top of the groove (indicated in the above Figure by L), or they will directly hit the top of the V-groove. In either situation, the cells will align in the groove, allowing for subsequent imaging.

In order for sufficient movement along the inclined surface of the groove, the surface should be flat and cells prohibited from sticking to the walls. To achieve a smooth precise V-groove design, known wafer etching technologies are used. However because of expense and optical requirements, silicon wafers are not appropriate, rather polydimethylsiloxane (PDMS) replica molding provides a composition that will meet these requirements. Compositions that will meet this criteria are also considered in the present invention. V-grooves, etched onto a silicon wafer, are the inverse of the eventual design, and provide the PDMS mold with the correct V-groove shape when poured onto the silicon mold. After curing, this shape is cut into dimensions that would allow replacement of the glass surface of the imaging chamber.

III. Longitudinal Variation of Chamber Height

Figure 4:
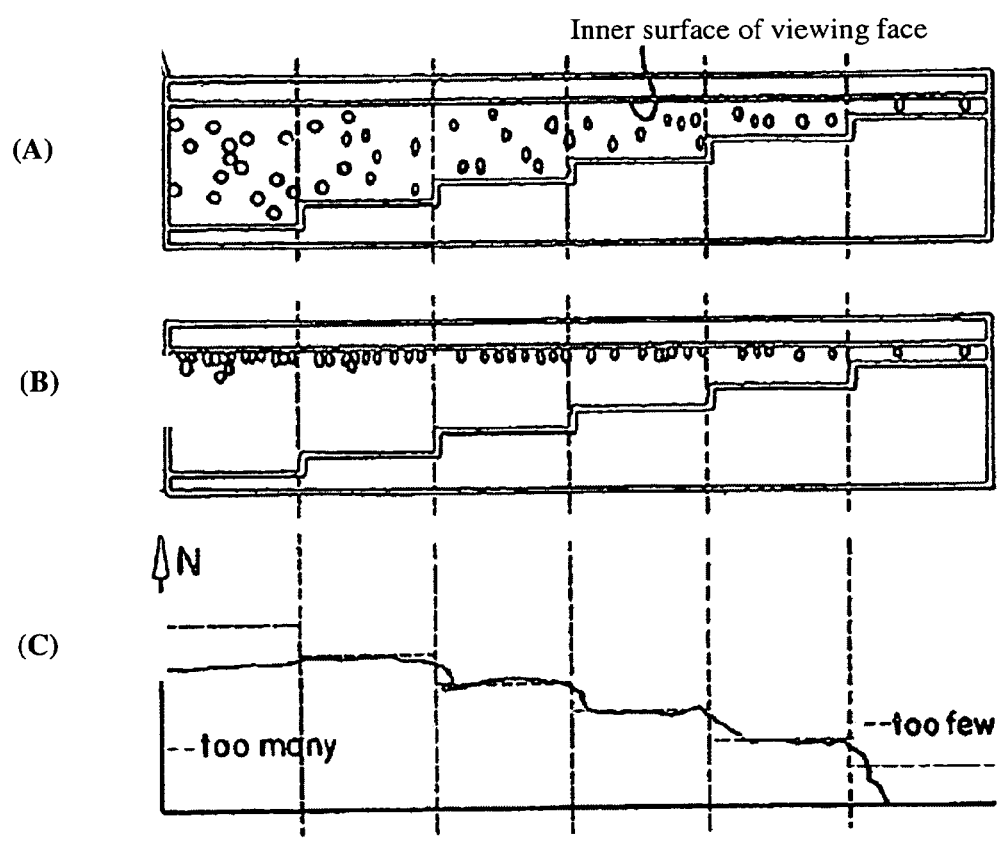
FIGS. 4A, 4B and 4C are successive schematic views showing a method of measuring particle density in a fluid having an unknown particle density.

The height of the chamber in concert with the concentration of the target entity determines the density of the distribution of target specimens collected at the collection surface of a vessel such as described above. To increase the range of surface collection densities which are acceptable for accurate counting and analysis, one can vary the height of the chamber to eliminate the need to dilute or concentrate the sample, for analysis of samples where the concentration may vary widely. In FIG. 4A, a cross section of a chamber is shown with a collection surface 1, and six compartments having different heights. Target cells are randomly positioned in the chamber. In FIG. 4B the same cross section is shown but now the cells have moved to the collection surface under the influence of the magnetic gradient. In the area of the highest chamber depth, the density of the cells is too high to be accurately measured, whereas in the area of the lowest chamber depth, too few cells are present to provide an accurate cell count. To further illustrate this principle, a histogram of the cell density along the collection surface is shown in FIG. 4C. Note that the number of cells in the area with the highest density is underestimated. The approach described here increases the range of concentrations which can be accurately measured as compared to the cell number measurements traditionally used in hematology analyzers and flow cytometers.

Figure 5:
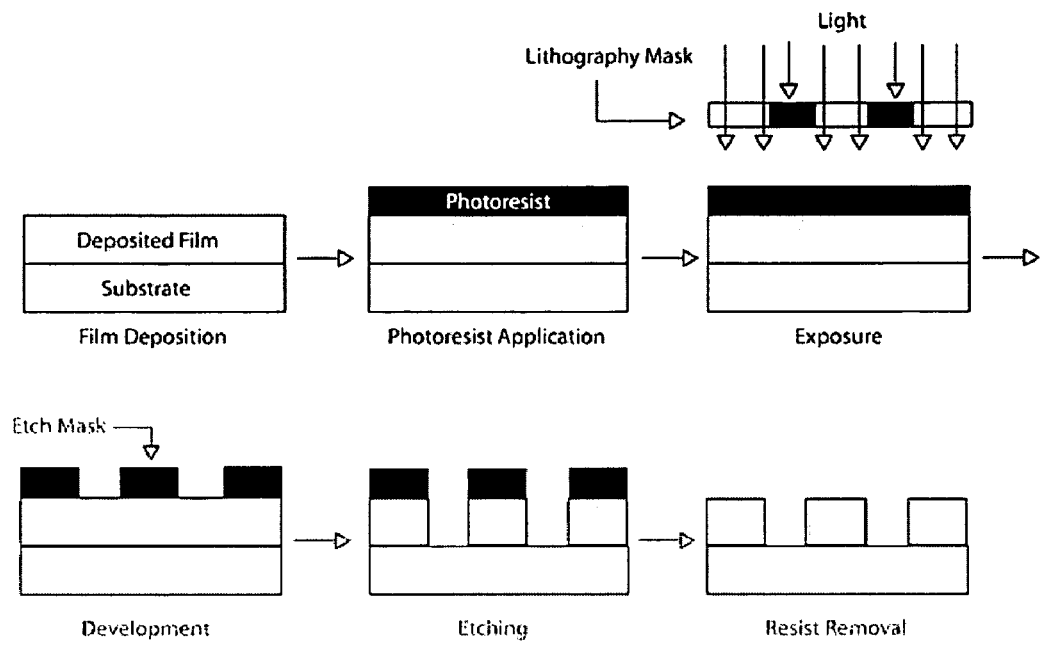
FIG. 5 is a schmatic of the proces steps in BHF etching. First, a thin layer of $SiO_2$ (500 nm) is grown on the wafer by steam oxidation. A layer of photoresist is added and then selectively removed at the parts where further etching should occur. This is done with a lithography mask that contains the patterns to be etched. Then the BHF is introduced, removing the $SiO_2$ at places were there is no etch mask (photoresist). Finally, the layer of photoresist is removed and only the thin layer of $SiO_2$ is left.

IV. Wafer Etching and PDMS Molding on Inner Surface of Viewing Face of Chamber Etching can be accomplished on any optically transparent material that can be used in the manufacture of the chamber. By example, silicon wafers can be used in etching because of the ease of precision, fine detail, and reproducability. Any material with similar characteristics and known in the art is considered in the present invention. Etching of the V-groove shapes uses two common etching techniques. First an etch mask that is needed to etch the grooves is created. This mask is created using BHF (Buffered Hydrofluoric acid) etching. The process of BHF etching is explained in FIG. 5. Once BHF etching is complete, thin layers of $SiO_2$ are left on the silicon wafer at places where no V-groove should be etched. Anisotropic etching is also used to etch the V-grooves. Here, KOH is used as etchant. When this process is applied to a properly orientated wafer, V-grooves are etched, limited by the crystal plane of the silicon wafer. Accordinly, a highly reproducible and constant etch angle is produced. The angle depends on the wafer orientation with one embodiment at a constant 35.26 degrees. Another technique is Deep Reactive Ion Etching (DRIE). By using this technique it is possible to etch structures with a high aspect ratio (ratio between length and width of the structure). DRIE cyclically alternates between etch and deposition steps forming scalloped sidewalls.

PDMS molding is used to obtain a positive imprint on the fabricated wafer. PDMS or Polydimethylsiloxane (Dow Corning (Sylgard 184, Dow Corning, Midland, Mich., USA) is a polymer containing the siloxane bond between Si (Silicon) and O (Oxygen). The polymers molecules are linked together to form longer polymers with an average number around 50 to 100.

Figure 6:
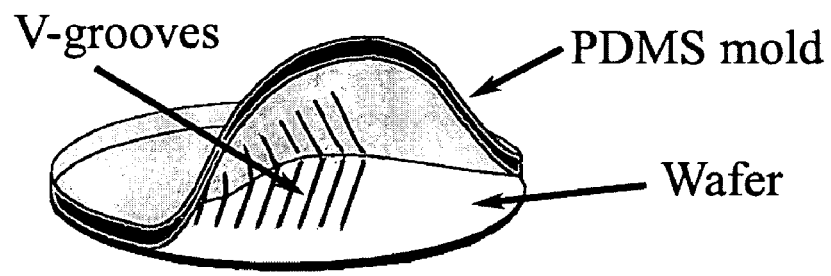
FIG. 6 is a schematic illustration of PDMS molding.
Figure 7:
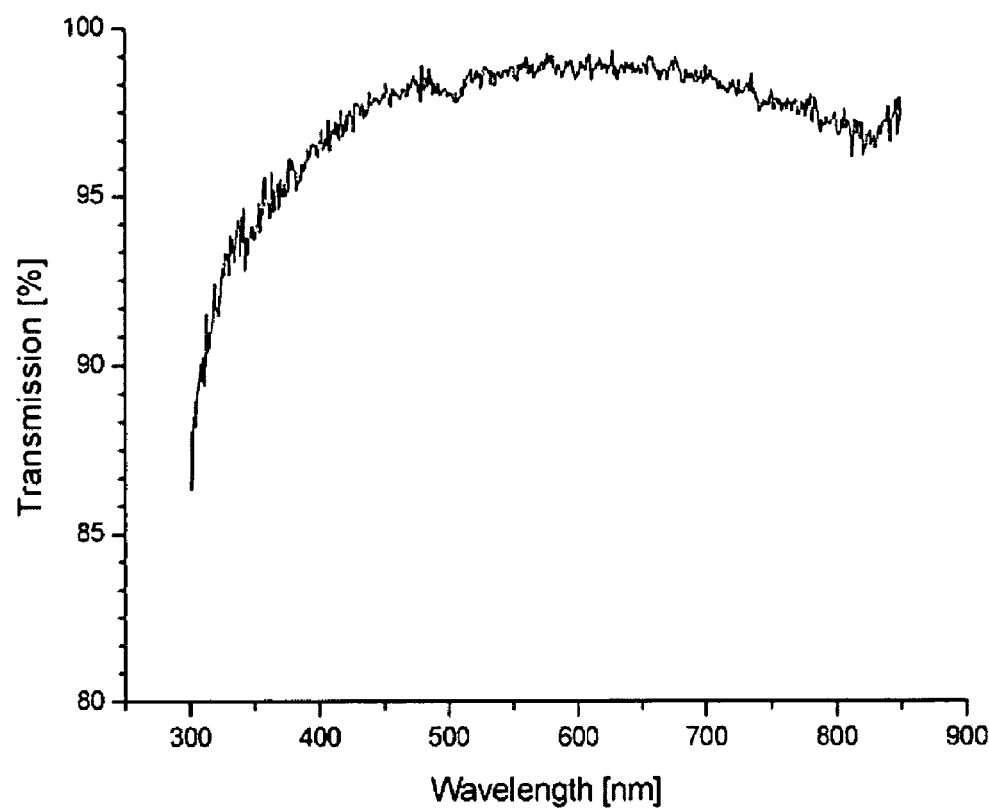
FIG. 7 is the transmission spectrum of a PDMS slab approximately 1 mm thick. Typical transmission ranges are from 95% to 99% between 400 and 900 nm.

The final PDMS is obtained with the addition of a cross-linker. The cross-linker connects with the polymers to form long networks of polymers, resulting in a clear, elastic, chemically inert, thermally stable material. After polymerization, the PDMS forms a clear flexible substance which adheres to very few materials and is not hygroscopic, thus preventing any sticking of cells to the sides due to the fact that PDMS adheres to very few materials. Furthermore, it is thermally stable and transparent from approximately 300 to 900 nm. These characteristics are all important for its use in a fluorescent imaging system and the transmission of visible light. FIG. 6 illustrates the relationship between the wafer, PDMS mold and the formation of the V-grooves. After formation the V-grooves are cut into the dimensions of the viewing face of the chamber. FIG. 7 depicts the transmission spectrum through the viewing surface.

V. Parameters of the V-Groove Viewing Surface and Examples of Use

Figure 8:
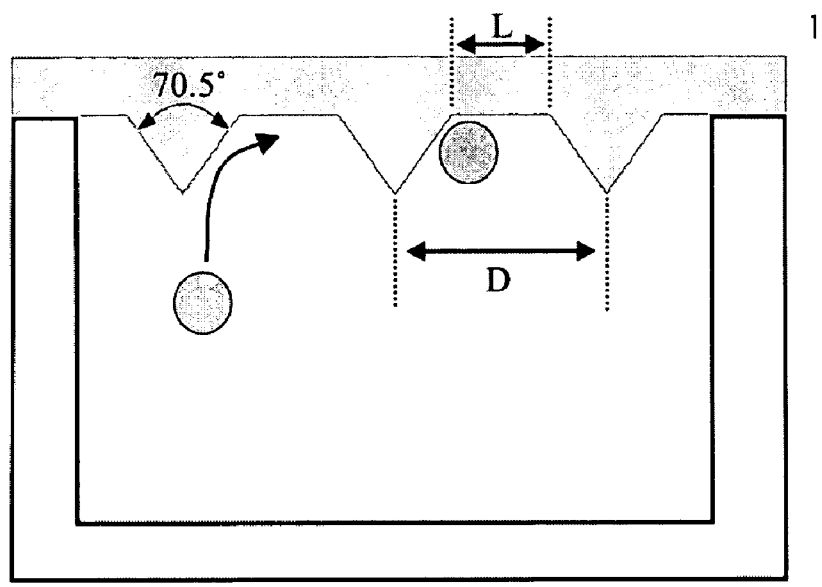
FIG. 8 shows a schematic illustration of V-grooves. L is the width of the horizontal area in the grooves and D is the spacing of the grooves. Cell alignment is shown with the arrow.

The prameters considered are shown in FIG. 8. L is the width of the flat horizontal area and D is the spacing of the grooves. Varying L will influence the alignment of the cells in the groove. If L is too big, cells may overlap or may be not perfectly aligned in the center. Misalignment influences scanning and imaging, complicating subsequent image analysis. As a consequence, the size of the laser spot has to be increased so as to match the increased area that has to be illuminated. The spacing of the grooves is controlled by D. This influences the maximum cell size and the number of cells that can be accommodated.

Figure 9:
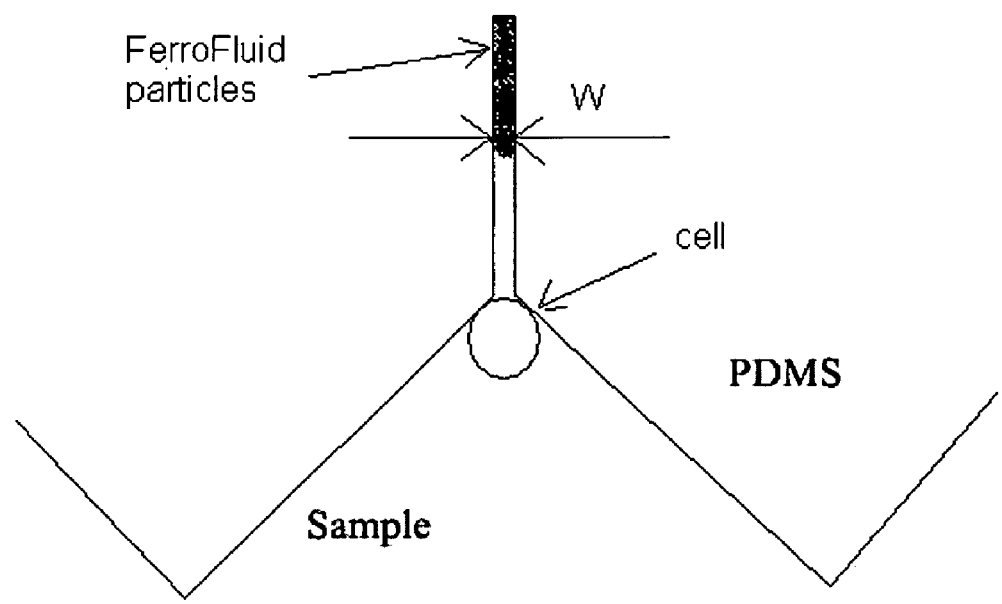
FIG. 9 shows a chimney-like design for removing the ferrofluid from the focal plane.

One possible example of a wafer design incorporates a chimney-like design (FIG. 9). This design accommodates the excess ferrofluid in solution to a position away from the cells. This design were fabricated using DRIE high aspect ratio etching. The width of the chimneys should be smaller than the smallest diameter of an interested cell.

Figure 10:
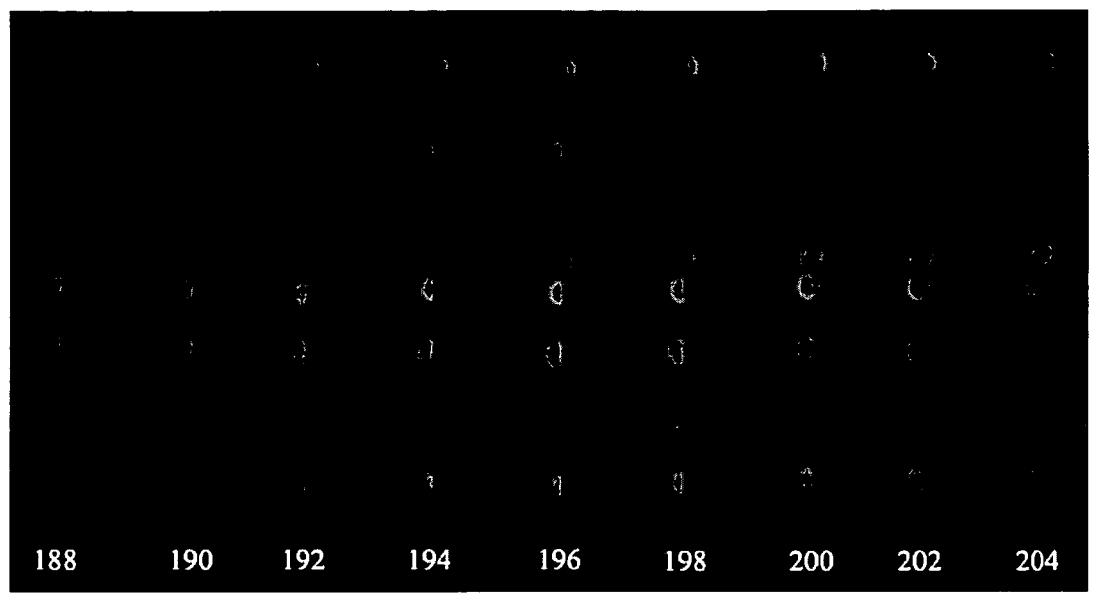
FIGS. 10A and 10B show the image of Hela cells in the V-grooves at several focal planes in DAPI and Cytokeratin-PE treated cells, respectively. Panel A shows several Hela cells aligned vertically for different points of focus within the cell. The numbers represent the values as obtained from imaging, indicating the point of focus in micrometers, using DAPI. Panel B shown the same with the phycoeurthrin (PE) labeled cytokeratin.
Figure 10:
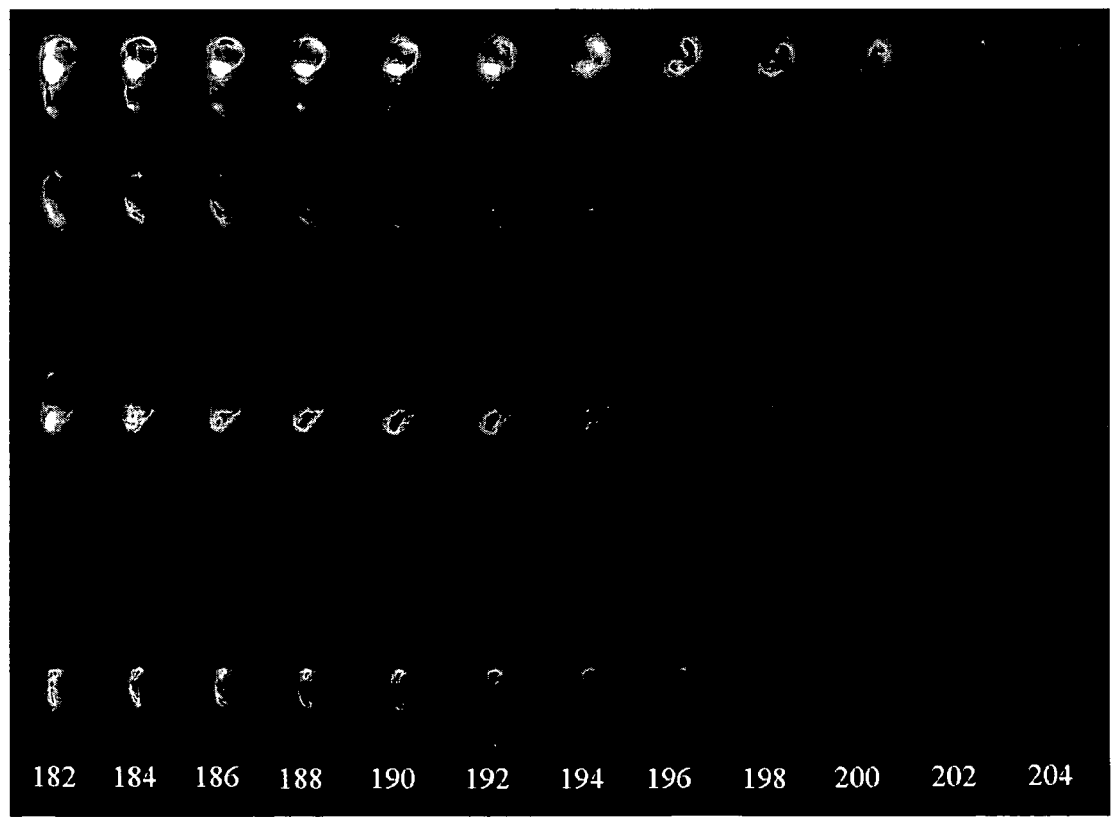

An example to depict the quality with which CTC's are imaged is demonstrated with Hela cells. Hela cells are labeled with Cytokeratin-PE (FIG. 10A) and DAPI (FIG. 10B) to fluorescently stain the nucleus and the cytoskeleton. These cells were tested in a chamber fitted with a V-groove structure on the viewing surface. Cells labeled with both cytokeratin-PE and DAPI were imaged at several focal points along the V-groove. At 200 µm, the top of the V-groove is in focus. Lower values indicate a lower point of focus.

EXAMPLE 1

With image cytometry such as in EasyCount, cells are usually randomly distributed on the analysis surface. To reduce imaging times, a PDMS (poly-dimethyl siloxane) microstructures were developed to align the cells in pre-defined areas and at the same time offer unobstructed imaging of the cells. These microstructures are produced by making PDMS molds of etched silicon wafers. The unique properties of PDMS make it an excellent material to use for these microstructures. It is optically transparent down to 300 nm, can easily be glued to supporting structures and is cost effective. Furthermore, structures can be replicated with sub-micron accuracy and adhesion of cells to the material is low.

Figure 11:
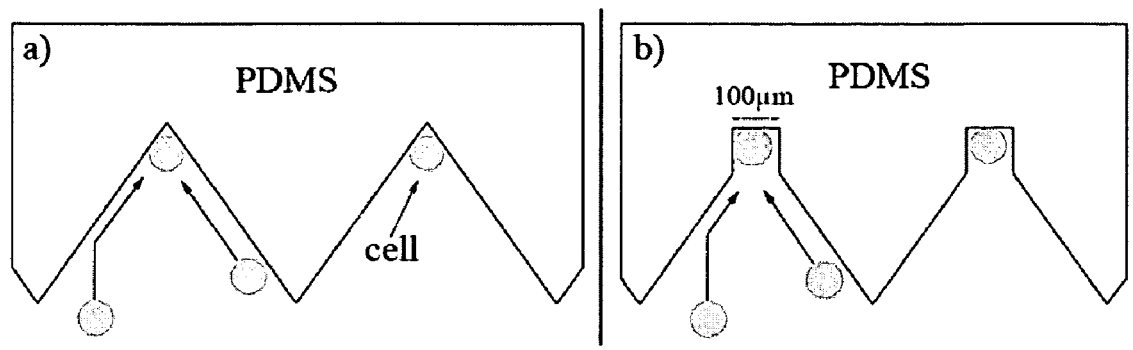
FIGS. 11A and 11B shows a diagram comparing microstructures. Panel A shows the V-groove structure formed from a PDMS mold. Panel B shows the foxhole structure having an improved image quality by allowing the cells to concentrate at the flat surface.

To align the cells, a force is needed; e.g. gravity or a magnetic force. The latter is used in the CellTracks® system, a Circulating Tumor Cell analysis system, to align cells in the microstructures. Characterization of these cells is done by scanning them with 4 homogenized laserspots. Essential properties of two microstructures like alignment and image quality were investigated using SKBR3 cells. They were immuno-magnetically labeled and aligned in the structures by a magnetic field. FIG. 11 gives an overview drawing of the two microstructures.

The first structure arranges the cells in a long line, like in Flow Cytometry, and is suited for cell counting. Cells are illuminated and imaged from the top of the structures shown in the figure. Image quality in the V-Groove is reduced by light diffraction at the tip of the V-Groove. The image quality is improved in the Foxhole structure were the cells are concentrated at a flat surface. Alignment efficiency of both structures is greater than 97%. Array orientation (2D grid) is also possible (not shown in figure) in square and hexagonal packing.

The V-Groove offers excellent alignment and good quantitative properties. The Foxhole microstructure offers good alignment and excellent image quality. It allows the illumination area to be matched to the channel width in the CellTracks system, thereby reducing scanning times by a factor of 3.

While certain of the preferred embodiments of the present invention have been described and specifically exemplified above, it si not intended that the invention be limited to such embodiments. Various modification may be made thereto without departing from the spirit of the present invention, the full scope of the improvements are delineated in the following claims.

The invention claimed is:

1. An improved method for optically analyzing microbiological specimens suspended in a fluid medium by magnetically labeling said specimens, which method comprises containing said magnetically-labeled specimens in a chamber having an optically-transparent viewing face having an interior surface, positioning said chamber into a magnetic field having a substantially uniform region of vertically-directed magnetic gradient and such that said chamber is located in said uniform region, collecting a uniformly-distributed layer of said magnetically-labeled specimens on the interior surface of said optically-transparent viewing face of said chamber, and conducting optical analysis of said magnetically-labeled specimens while maintaining said magnetically-labeled specimens collected on said interior surface of said optically-transparent viewing face of said chamber, and wherein said improvement comprises collecting said uniformly-distributed layer of said magnetically-labeled specimens within preformed V-grooves on said interior surface of said optically-transparent viewing face of said chamber.

2. The method of claim 1 wherein said V-grooves contain a chimney-shaped component in order to allow unbound magnetic label to partition above a focal plane for said optical analysis.

3. The method of claim 1 wherein said fluid medium containing said magnetically-labeled specimens has a predetermined dilution of said magnetically-labeled specimens such that said dilution provides for optimum alignment of said magnetically-labeled specimens along inner surface of viewing face.

4. The method of claim 1 wherein said specimens is from a group consisting of epithelial cells, circulating tumor cells, endothelial cells, fungal cells, bacterial cells, and combinations thereof.

5. The method of claim 1 wherein said V-grooves are microstructures shaped as foxholes having a flat surface for concentrating magnetically-labeled specimens.

6. An improved apparatus for observing magnetically responsive microscopic specimens suspended in a fluid member, said apparatus having a fluid containing chamber with an optically-transparent viewing face having an interior surface, a ferromagnetic capture structure supported on the interior surface of said optically-transparent viewing face, magnetic means for inducing an internal magnetic gradient in the vicinity of said ferromagnetic capture structure, whereby said magnetically responsive specimens are immobilized along said optically-transparent viewing face adjacent to said capture structure and an electrical conductor means supported on said optically-transparent viewing face for enabling electrical manipulation of said immobilized specimens, wherein said improvement comprises a collection means having preformed V-grooves on the inner surface of said optically-transparent viewing face to allow for uniform distribution of said specimens during optical analysis.

7. The improved apparatus of claim 6 wherein said V-grooves contain chimney-shaped components for separating small magnetically responsive entities from larger magnetically responsive specimens during optical analysis.

8. The improved apparatus of claim 6 wherein said specimen is from a group consisting of epithelial cells, circulating tumor cells, endothelial cells, fungal cells, bacterial cells and combinations thereof.

9. The improved apparatus of claim 6 wherein said V-grooves are microstructures shaped as foxholes having a flat surface for concentrating magnetically-labeled specimens.

10. The improved apparatus of claim 6 wherein said specimens is from a group consisting of epithelial cells, circulating tumor cells, endothelial cells, fungal cells, bacterial cells, and combinations thereof.

11. An apparatus for observing magnetically responsive microbiological specimens suspended in a fluid member, comprising:
    a. a fluid containing chamber with an optically-transparent viewing face having an interior surface;
    b. a ferromagnetic capture structure supported on the interior surface of said optically-transparent viewing face;

c. an externally applied magnetic gradient; and d. collection means having an etched surface on said interior surface of said optically-transparent viewing face to allow for uniform distribution of said specimens during optical analysis.

12. The apparatus of claim 11 whereby said etched surface contains V-grooves for optimum alignment of said specimens during optical analysis.

13. The apparatus of claim 12 whereby said V-grooves contain chimney-shaped components for separating small magnetically responsive entities from larger magnetically responsive specimens during optical analysis.

14. The apparatus of claim 11 whereby said inner surface contains foxholes grooves having a flat surface for concentrating magnetically-labeled specimens for optimum alignment of said specimens during optical analysis.

* * * * *

UNITED STATES PATENT AND TRADEMARK OFFICE
CERTIFICATE OF CORRECTION

| | | |
|---|---|---|
| PATENT NO. | : 7,666,308 B2 | Page 1 of 1 |
| APPLICATION NO. | : 11/447562 | |
| DATED | : February 23, 2010 | |
| INVENTOR(S) | : Scholtens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 561 days.

Signed and Sealed this

Twenty-sixth Day of October, 2010

David J. Kappos
*Director of the United States Patent and Trademark Office*